United States Patent [19]

Bryant

[11] Patent Number: 5,078,703
[45] Date of Patent: Jan. 7, 1992

[54] CATHETER ADAPTER AND RETAINER

[75] Inventor: Peter L. Bryant, Lake Forest, Ill.

[73] Assignee: Abbott Laboratories, Abbott Park, Ill.

[21] Appl. No.: 421,210

[22] Filed: Oct. 13, 1989

[51] Int. Cl.⁵ .............................................. A61M 25/00
[52] U.S. Cl. ..................................... 604/283; 604/243
[58] Field of Search ................. 604/165, 177–180, 604/280, 283, 411, 905, 240, 243; 128/912

[56] References Cited

U.S. PATENT DOCUMENTS

| 3,630,195 | 12/1971 | Santomieri | 604/180 |
|---|---|---|---|
| 4,006,744 | 2/1977 | Steer | 604/283 |
| 4,397,641 | 8/1983 | Jacobs | 604/180 |
| 4,419,094 | 12/1983 | Patel | 604/165 |
| 4,659,329 | 4/1987 | Annis | 604/180 |
| 4,675,007 | 6/1987 | Terry | 604/283 |
| 4,723,948 | 2/1988 | Clark et al. | 604/283 |

Primary Examiner—John D. Yasko
Assistant Examiner—Anthony M. Gutowski
Attorney, Agent, or Firm—Clifford A. Dean; A. Nicholas Trausch

[57] ABSTRACT

An adapter and retainer for field assembly to the proximal end of a catheter in the form of a plastic clip having a length of flexible tubing mounted thereon into which the end of the catheter is inserted after which two jaws of the clip are locked together to sealingly compress the flexible tubing about the catheter, the catheter also being wrapped one or more times about reel formations provided on the clip and then snapped into retention grooves provided on the clip whereby to absorb any force applied to the catheter which would otherwise tend to separate the catheter from the clip.

5 Claims, 3 Drawing Sheets

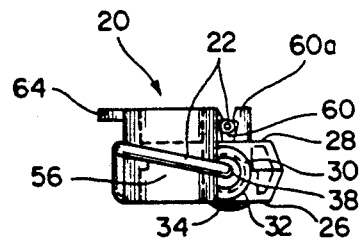
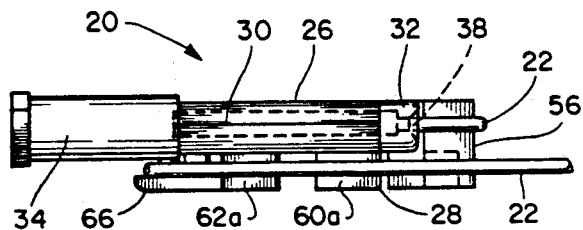
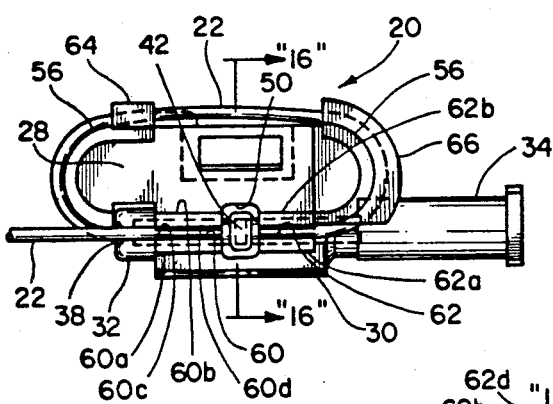
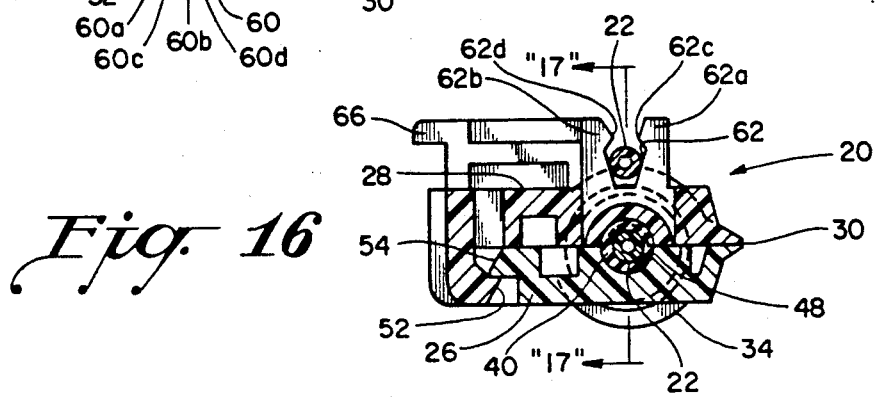
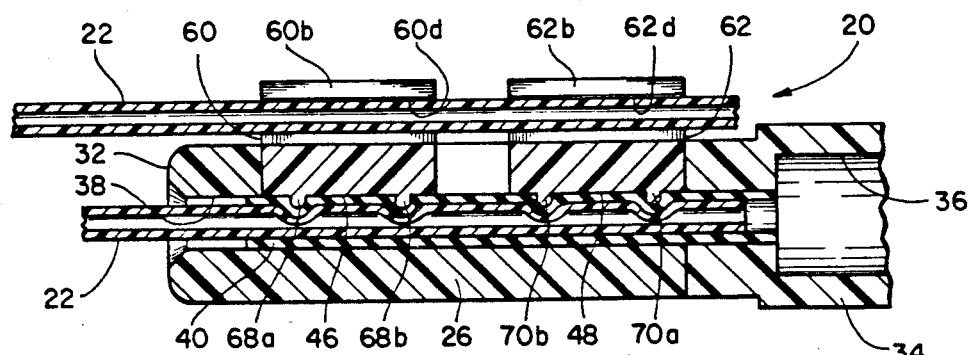

CATHETER ADAPTER AND RETAINER

BACKGROUND OF THE INVENTION

This invention relates to a medical device such as an adapter that is field assembled, as during or following surgery or child birth, on the proximal end of a catheter, such as an epidural catheter used during child birth. An adapter of this general type is disclosed in U.S. Pat. No. 4,006,744, which issued Feb. 8, 1977 to the assignee of this application. The adapter of the foregoing patent is characterized by a pair of clamping jaws which are adapted to be clampingly closed upon a length of flexible tubing mounted in the adapter and into one end of which the proximal end of a catheter has been inserted whereupon the flexible tubing is sealingly compressed about the catheter, the tubing also being in communication at its opposite end with a luer tapered sleeve provided on the adapter.

The adapter of the foregoing patent provides a very effective sealed connection thereof to the proximal end of a catheter and which, because of its novel simplicity, is easily field assembled thereto. Such adapters are often pinned or clipped to a patients hospital gown. The only problem of any consequence encountered during use of the catheter adapter of the foregoing patent is that, on occasion, a patient's movements, or some other cause, may result in a very strong pulling or separation force being applied to the catheter and disconnection of the catheter from the adapter. Moreover, this phenomenon is common to all types of field assembled adapters. Such disconnection risks contamination to the patient and presents a nuisance to the hospital staff. Applicant's improved catheter adapter and retainer overcomes this very critical problem by providing a novel supplementary retention means on the adapter.

SUMMARY OF THE INVENTION

The present invention is directed to an improved catheter adapter of the clip type wherein the proximal end of the catheter is inserted into one end of a length of flexible tubing mounted in the adapter after which two hinged portions of the adapter clip are clamped together with the flexible tubing being compressed onto the proximal end of the catheter to provide a sealed connection therebetween. The improvement comprises the addition of supplemental retention means for the adapter in addition to the retention force developed by compression of the flexible tubing retention force developed by compression retention force is limited, of course, by the crush strength of the catheter.

The supplemental retention means, as will be clarified hereinafter, effectively multiplies the compression retention force against any separation or pulling force that may be exerted on the catheter. This supplemental retention means is characterized by friction on reel formations provided on opposite sides of the adapter clip with one reel formation being immediately adjacent the entry point of the catheter into the adapter clip and by resilient quipping groove formations disposed between the reel formations into which the catheter is received. The reel and groove formations provide a self locking arrangement for the catheter relative to the adapter when the catheter is retained in the clip closure, wrapped on the reels and secured in the groove. The groove holds the catheter to the reel when no separation force is present. Any and all separation forces between the catheter and the adapter are retained by the combined retention force of the clip closure of the adapter and the friction of the catheter to the adapter reels.

While the preferred embodiment entails using a frictional wrap to multiply the retention force of a clip type adapter, the use of frictional wrapping on the bodies of all types of adapters would likewise multiply their retention forces. In similar fashion, the groove formations herein described are preferred embodiments for holding the catheter to the frictional reels when no separation forces are applied. Other groove designs and other holding means are also envisioned.

BRIEF DESCRIPTION OF THE DRAWINGS

FIG. 13 is an opposite side elevational view of the adapter and retainer clip similar to FIG. 8 but after mounting of same on the catheter;

FIG. 14 is a rear elevational view thereof similar to FIG. 9;

FIG. 15 is a top plan view thereof similar to FIG. 11;

FIG. 16 is an enlarged traverse sectional view taken generally along line 16—16 of FIG. 15; and FIG. 17 is a fragmentary longitudinal sectional view taken . generally along line 17—17 of FIG. 16.

DESCRIPTION OF THE PREFERRED EMBODIMENT

Figure 1:
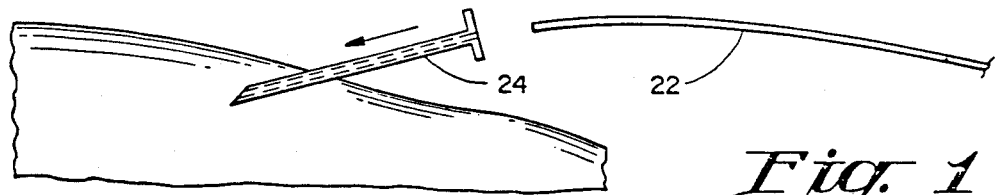
FIG. 1 is a diagrammatic view of an epidural cannula being inserted into a patient.
Figure 2:
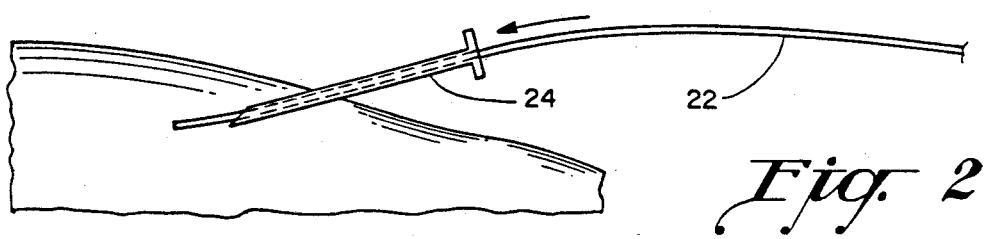
FIG. 2 is a diagrammatic view of the distal end of an epidural catheter being inserted into the epidural cavity of the patient through the cannula.
Figure 3:
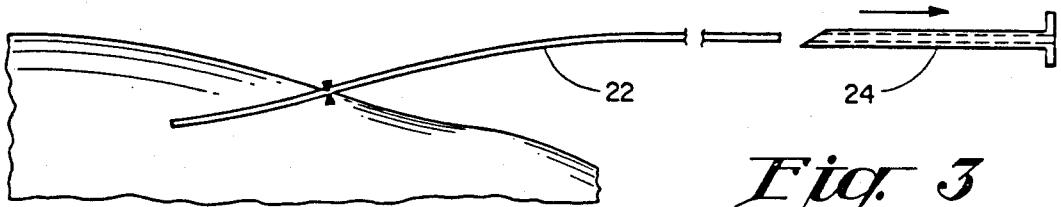
FIG. 3 is a diagrammatic view of the cannula being removed from the patient over the proximal end of the catheter, after which the catheter may be secured to the patient, as by taping.

Referring now to the drawings, FIGS. 1-5 graphically illustrate the field assembly of an epidural catheter adapter and retainer 20 embodying the invention to an epidural catheter 22. As illustrated, a cannula 24 is first inserted into the patient's epidural space (FIG. 1) after which the distal end of the flexible epidural catheter 22 is inserted into the epidural space through the hollow cannula 24 (FIG. 2). The cannula 24 may then be withdrawn from the patient over the free proximal end of the catheter 22 (FIG. 2), after which the epidural catheter adapter and retainer 20 may be assembled to the proximal end of the epidural catheter 22 in a manner to be described hereinafter.

With reference to FIGS. 6-17, the catheter adapter and retainer 20, the body of which is preferably molded in one piece rom a suitable plastic material and may be referred to hereinafter as a plastic clip, is characterized by two oppositely positioned jaw portions 26 and 28 which are connected to one another by a weakened living hinge portion 30. The jaw portion 26 has formed on one side thereof a catheter entry port formation 32 and, on the opposite side thereof, a sleeve formation 34 having a luer-tapered bore 36 which is axially aligned with a catheter entry passage 38 provided in the entry port formation 32, the axially aligned bore 36 and passage 38 being disposed parallel to thee hinge portion 30.

Supported on the jaw portion 26 and having its opposite ends sealingly received in the inner ends of the luer-tapered bore 36 and the entry passage 38 is a length of flexible tubing 40 formed of rubber or rubber like material. A strap like retainer formation 42 for the tubing 40 is provided on the jaw portion 26 approximately midway between the opposite sides thereof, the length of tubing 40 extending under the strap like retainer formation 42.

The jaw portion 28 is provided on its inner surface with a pair of semi cylindrical grooves 46 and 48 which are axially aligned, spaced apart, and disposed parallel to the length of flexible tubing 40. The axially aligned axes of the grooves 46 and 48 and the axis of the length of tubing 48 are spaced equidistantly from the hinge 30 on opposite sides thereof whereby when the two jaw portions 26 and 28 are closed together, the grooves 46 and 48 fit over portions of the flexible tubing 40 on opposite sides of the strap-like retainer formation 42. An opening 50 is provided in the jaw portion 28 between the spaced apart grooves 46 and 48 to accommodate the strap like retainer formation 42 when the two jaw portions 26 and 28 are closed together. The radii of the semi-cylindrical grooves 46 and 48 are slightly less than outer radials of the flexible tubing 40 whereby when the two jaw portions 26 and 28 are closed together, the grooves 46 and 48 exert a compressive force on the portions of the flexible tubing 40 engaged thereby for reasons that will be further discussed hereinafter. As the proximal end of the epidural catheter 22 is to be inserted through the catheter entry passage 38 and into the adjacent end of the length of flexible tubing 40 before the two jaw portions 26 and 28 are closed together, this compressive force exerted on the flexible tubing 40 by the grooves 46 and 48 serves not only to provide a fluid tight seal between the catheter 22 and the tubing 40 but also as a retention force against longitudinal separation of the catheter 22 from the plastic clip 20.

The second jaw portion 28 is provided with a hook like latching member 52 which, when the two jaw portions 26 and 28 are closed together, snaps over an edge 54 on the first jaw portion 26 to lock the two jaw portions 26 and 28 together. When the jaws 26 and 28 are locked together, the opposite outer surfaces of the closed clip are generally parallel to one another to facilitate taping or otherwise attaching the generally flat clip 20 to a patient's body or hospital gown.

The second jaw portion 28 is also provided with Supplemental retention means in the form of a pair of curved reel formations 56 and 58 and a pair of retention grooves 61 and 62, all of which are provided on the second jaw portion 28. As illustrated in the drawings, the reel formation 56 is provided at the catheter side of the plastic clip 20 and the reel formation 58 is provided at the luer tapered sleeve side of the clip 20. The two reel formations 56 and 58 are rounded and define, as best illustrated in plan view in FIGS. 11 and 15, a non-continuous race-track shaped configuration. The outer edges of the two reel formations 56 and 58 are provided, respectively, which normally disposed upstanding side rail formations 64 and 66. When the two jaw portions 26 and 28 are locked together, a portion of the curved reel formation 56 is immediately adjacent the catheter entry passage 38 for a reason that will be discussed hereinafter. The retention grooves 60 and 62 are defined by spaced apart wall formations 60a, 60b and 62a, 62b which project normally from the outer surface of the second jaw portion 28 in back to back alignment with the semi cylindrical grooves 46 and 48. As best illustrated in FIG. 15, the retention, grooves 60 and 62 define a "straight away" portion of the aforesaid race track shaped configuration.

Figure 4:
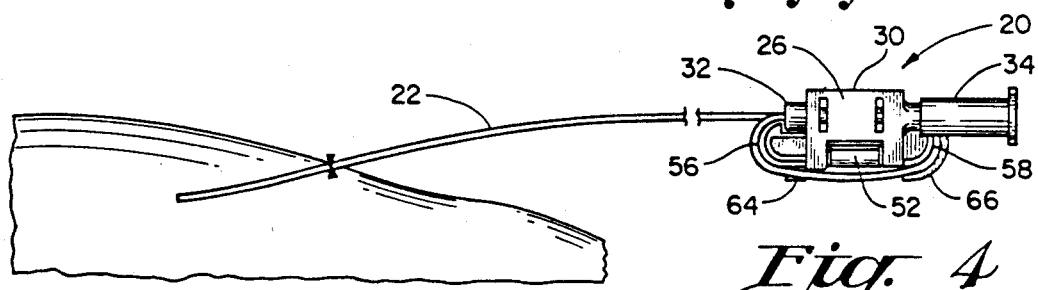
FIG. 4 is a diagrammatic view illustrating completion of field assembly of the catheter adapter and retainer of the present invention to the proximal end of the catheter.
Figure 5:
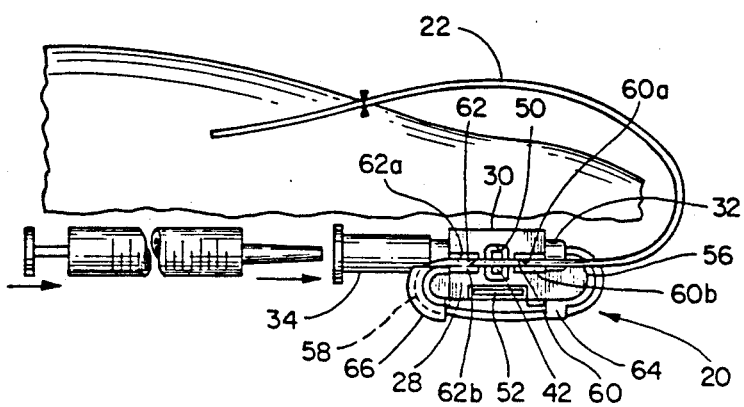
FIG. 5 is a diagrammatic view illustrating repositioning of the adapter and retainer relative to the patient to permit use therewith of a hypodermic syringe having a male luer taper connection provided thereon.
Figure 6:
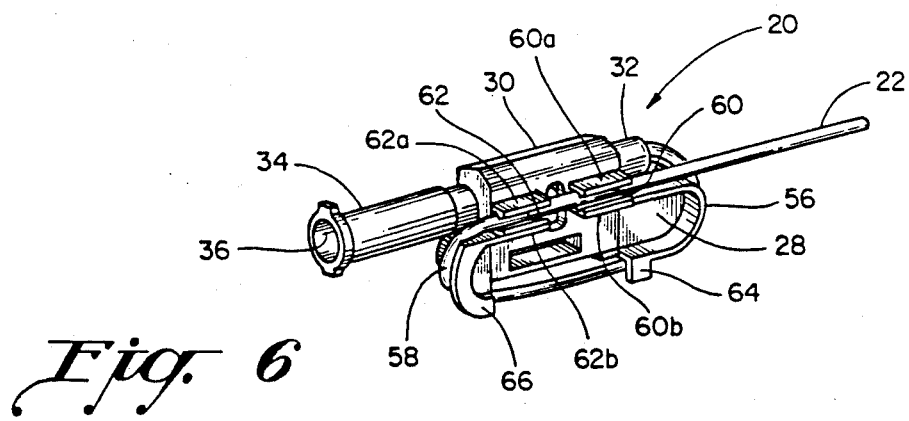
FIG. 6 is a perspective view of the adapter and retainer embodying the invention and shown in FIGS. 4 and 5 mounted on the epidural catheter.
Figure 7:
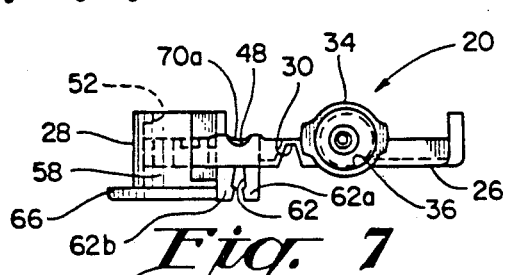
FIG. 7 is a side elevational view of the opened up adapter and retainer prior to mounting of same on the catheter.
Figure 8:
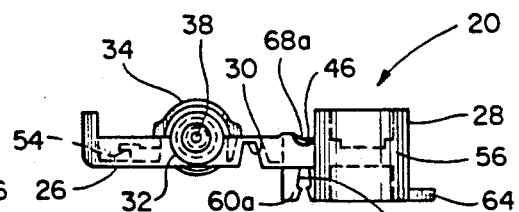
FIG. 8 is an opposite side elevational view thereof.
Figure 9:
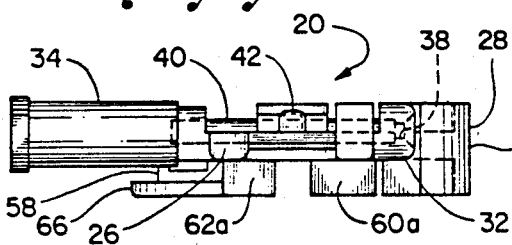
FIG. 9 is a rear elevational view thereof.
Figure 10:
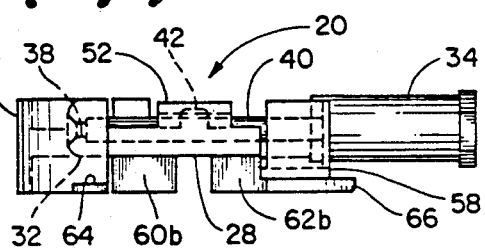
FIG. 10 is a front elevational view thereof.
Figure 11:
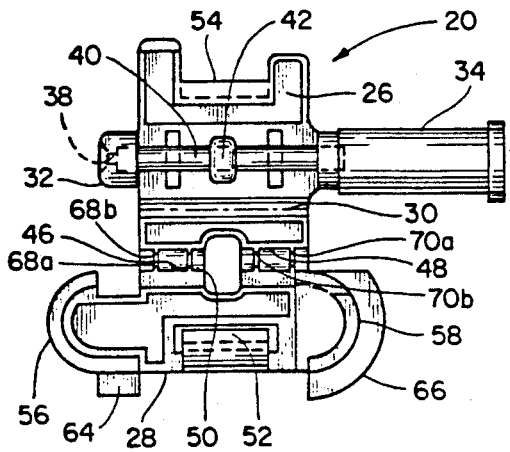
FIG. 11 is a top plan view thereof.
Figure 12:
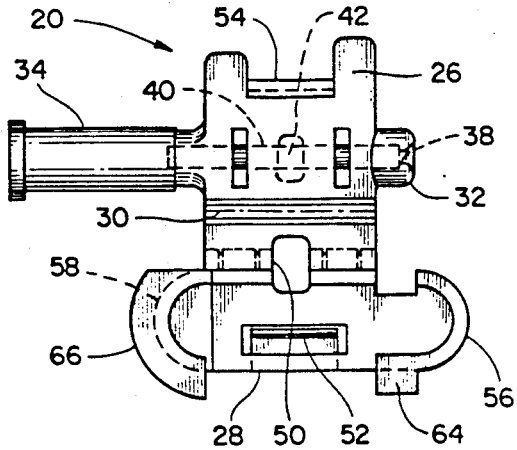
FIG. 12 is a bottom plan view thereof.

To field assemble the plastic clip 20 to the proximal end of a catheter, such as the epidural catheter 22 in FIG. 4, the end of the catheter 22 is inserted into t ca entry passage 38 of the clip 21 and into the adjacent end of the length of flexible tubing 40. The two jaw portions 26 and 28 are then closed together and locked, as previously described herein, whereupon compressive pressure is applied to the flexible tubing 40 to provide the aforesaid sealing and retention forces on the catheter 22. It is noted that the foregoing compressive pressure is limited by the crush strength of such caters and the ability of the assembler to achieve but not exceed width crush strength limit. Therefore perfect retention normally cannot be achieved by such evenly distributed compressive pressure.

As is best illustrated in FIG. 17, one structural improvement that improves the retention force on the catheter 22 is the provision of a pair of raised transverse ribs 68a and b and 70a and b in the pair of semi cylindrical grooves 46 and 48.

However, an even more effective means of withstanding any separation force between the catheter 22 and the clip 20 is the frictional effect of the reel formations 56 and 58 on the catheter 22 in combination with the aforesaid compression of the tubing 40 about the catheter 22 by the clip action of the adapter 20. After insertion of the proximal end of the catheter 22 into the catheter entry passage 38 of the clip 20 and into the length of flexible tubing 40 and latching of the clip 20, the catheter 22 is wrapped one or more times about the race-track shaped configuration defined by the reel formations 56 and 58 and then snapped into the retention grooves 60 and 62, the retention groove wall formations 60a and b and 62a and b being provided with inwardly directed detent formations 60c and d and 62 c and d, respectively, as best illustrated in FIG. 16. With this supplemental retention system, any force applied to the catheter 22 tending to separate the catheter 22 from the plastic clip 20 as seen by this combined retention system rather than only by the portion of the catheter 22 which enters the catheter entry passage 38 of the plastic clip 20.

The retention grooves 60 and 62 are of particular importance for holding the wound catheter 22 on the reel formations 56 and 58 during the absence of a separation force on the catheter 22.

The preferred form of an adapter clip 20 illustrated in FIGS. 4-17 permits one to elect to utilize the catheter wrap-around technique for supplemental retention force on the catheter after closing of the clip 20 on the catheter even if it was initially determined that no supplemental retention force would be required.

While there has been shown and described a preferred embodiment of the invention, it will be obvious to those skilled in the art that changes and modifications may be made without departing from the invention, and it is intended by the appended claims to cover all such changes and modifications as fall within the true spirit and scope of the invention.

I claim:

1. A catheter adapter and retainer comprising a formed plastic clip having a pair of jaws hingedly connected together and means for automatically latching the two jaws together when closed, a length of flexible tubing mounted on the inner surface of one of said jaws, a catheter entry passage in said clip for inserting the end of a catheter therethrough and into one end of said flexible tubing prior to closing of said jaw, a second passage in said clip in communication with said tubing for placing the catheter in fluid communication with another device, semi-cylindrical compressing means provided on the inner surface of the other jaw for compressing said flexible tubing about said catheter end when said jaws are latched together whereby to provide both a sealing force and a retention force on said catheter, and supplemental catheter retention means on the outer surface of said clip for providing supplemental retention of catheter in said clip.

2. The catheter adapter and retainer of claim 1 wherein said supplemental catheter retention means comprises race track shaped rounded reel means immediately adjacent to said catheter entry passage around which said catheter may be wrapped one or more times as it exits said entry passage and retention groove means associated with said rounded reel means into which said wrapped catheter may be snapped to provide self-locking thereof relative to said clip.

3. A catheter adapter and retainer comprising a formed plastic clip having a pair of jaws hingedly connected together to define a hinge connection, a length of flexible tubing mounted on the inner surface of one of said jaws, a catheter entry passage in said clip in communication with one end of said length of flexible tubing whereby an end of a catheter may be inserted into said one end of said length of tubing through said catheter entry passage, a second passage in said clip in communication with said tubing for placing the catheter in fluid communication with anther device, means on the inner surface of the other one of said jaws for compressing said flexible tubing about said catheter end when said jaws are closed to provide both a sealing force and a retention force on said catheter, rounded reel means provided on the outer surface of said clip immediately adjacent to said catheter entry passage about which said catheter may be wrapped one or more times as it exits said entry passage, and gripping slot means associated with said reel means into which said wrapped catheter may be snapped to provide self-locking thereof relative to said clip, said reel means and said gripping slot means being adapted to provide a supplemental retention force for said catheter to minimize the likelihood of said catheter being separated from said clip.

4. A catheter adapter and retainer comprising a formed plastic clip having first and second jaws hingedly connected together to define a hinge connection having a longitudinal axis, a length of flexible tubing disposed on said first jaw in parallel alignment with said hinged connection and with its opposite end supported in first and second bolted end mounts provided on said first jaw, a proximal end of a catheter, whose distal end is adapted for insertion into a patient, being insertable into said length of tubing through said first one of said end mounts, said second bolted end mount being in communication with said tubing for placing the catheter in fluid communication with another device, clamping means on said second jaw compressibly engageable with said flexible tubing when said first and second jaws are closed together for sealingly retaining said proximal end of said catheter in said length of flexible tubing and in said clip, a rounded reel formation provided on one of said jaws adjacent said first one of said end mounts and having catheter-gripping groove means provided thereon whereby the portion of said catheter projecting from said first one of said end mounts may be wrapped one or more times around said reel formation and then anchored in said gripping groove means to multiply any retention force on said catheter being applied to the distal end portion beyond the sealingly retained in said length of flexible tubing and said clip alone, a longitudinal axis of said reel formation extending parallel to said axis of said hinge connection.

5. The catheter adapter and retainer of claim 4 wherein said first jaw is provided with a strap-like retainer which extends over said flexible tubing approximately midway between the ends thereof and wherein said clamping means on said second jaw is characterized by a pair of longitudinally spaced apart semi-cylindrical clamping members which are adapted to compressibly engage said length of flexible tubing on opposite sides of said strap-like retainer.

* * * * *

UNITED STATES PATENT AND TRADEMARK OFFICE
CERTIFICATE OF CORRECTION

PATENT NO. : 5,078,703

DATED : Jan. 7, 1992

INVENTOR(S) : PETER L. BRYANT

It is certified that error appears in the above-identified patent and that said Letters Patent is hereby corrected as shown below:

Column 1, line 3; Replace "child birth" with --child-birth--

Column 1, line 4: Replace "child birth" with --child-birth--

Column 1, line 14: Replace "luer tapered" with --luer-tapered--

Column 1, line 19: Replace "field assembled" with --field-assembled--

Column 1, lines 46 & 47: Replace "flexible tubing retention force developed by compression" with --flexible tubing onto the catheter, which compressive--.

Column 1, line 57: Replace "quipping" with --gripping--

Column 2, line 4: Replace "clip type" with --clip-type--

Column 2, line 14: Replace "diagrammatic" with --diagramatic--

Column 2, line 16: Replace "diagrammatic" with --diagramatic--

Column 2, line 19: Replace "diagrammatic" with --diagramatic--

Column 2, line 23: Replace "diagrammatic" with --diagramatic--

Column 2, line 27: Replace "diagrammatic" with --diagramatic--

Column 2, line 30: Replace "luer taper" with --luer-taper--

Column 2, line 51: Replace "taken . generally" with --taken generally--

Column 3, line 3: Replace "rom" with --from--

Column 3, line 13: Replace "thee" with --the--

Column 3, line 17: Replace "rubber like" with --rubber-like--

Column 3, line 18: Replace "strap like" with --strap-like--

Column 3, line 21: Replace "strap like" with --strap-like--

Column 3, line 24: Replace "semi cylindrical" with --semi-cylindrical--

Column 3, line 28: Replace "tubing 48 are" with --tubing 40 are--

UNITED STATES PATENT AND TRADEMARK OFFICE
CERTIFICATE OF CORRECTION

PATENT NO. : 5,078,703

DATED : January 7, 1992

INVENTOR(S) : Peter L. Bryant

It is certified that error appears in the above-identified patent and that said Letters Patent is hereby corrected as shown below:

Column 3, line 35: Replace "strap like" with --strap-like-- .

Column 3, line 37-38: Replace "less than outer radials" with --less than the outer radius--.

Column 3, line 48-49: Replace "fluid tight" with --fluid-tight--.

Column 3, line 52: Replace "hook like" with --hook-like-- .

Column 3, line 64: Replace "grooves 61 and" with --grooves 60 and-- .

Column 3, line 68: Replace "luer tapered" with --luer-tapered--

Column 4, line 13: Replace "back to back" to --back-to-back-- .

Column 4, line 15: Replace "the retention, grooves" with --the retention grooves--.

Column 4, line 16: Replace "race track" with --race-track-- .

Column 4, line 20: Replace "into t ca" with --into the catheter-- .

Column 4, line 28: Replace "caters" with --catheters-- .

Column 4, line 29: Replace "width" with --said-- .

Column 4, line 36 & 37: Replace "semi cylindrical" with --semi-cylindrical--.

Column 4, line 56: Replace "clip 20 as seen" with --clip 20 is seen-- .

Column 5, line 28 (claim 1): Replace "of catheter in said clip" with --of said catheter in said clip-- .

Column 5, line 31 (claim 2): Replace "race track" with --race-track-- .

UNITED STATES PATENT AND TRADEMARK OFFICE
CERTIFICATE OF CORRECTION

PATENT NO. : 5,078,703
DATED : January 7, 1992
INVENTOR(S) : Peter L. Bryant It is certified that error appears in the above-identified patent and that said Letters Patent is hereby corrected as shown below:

Column 5, line 48: Replace "anther" with --another--.
Column 6, line 18: Replace "bolted" with --bored--.
Column 6, line 22: Replace "bolted" with --bored--.

Signed and Sealed this

Tenth Day of August, 1993

Attest:

MICHAEL K. KIRK

*Attesting Officer*    Acting Commissioner of Patents and Trademarks